United States Patent [19]

Bannister

[11] 4,240,891

[45] Dec. 23, 1980

[54] OXYGEN SENSORS

[75] Inventor: Michael J. Bannister, Glen Waverley, Australia

[73] Assignee: Commonwealth Scientific and Industrial Research Organization, Campbell, Australia

[21] Appl. No.: 46,126

[22] Filed: Jun. 6, 1979

[30] Foreign Application Priority Data

Jun. 6, 1978 [AU] Australia ............... PD4616

[51] Int. Cl.$^3$ .............. C04B 35/48; G01N 27/58
[52] U.S. Cl. ................ 204/195 S; 204/1 T; 106/62
[58] Field of Search ............. 106/57, 62, 58, 55; 204/195 S, 1S, 295

[56] References Cited

U.S. PATENT DOCUMENTS

| | | | |
|---|---|---|---|
| 3,567,472 | 3/1971 | Bratton | 106/62 X |
| 3,875,277 | 4/1975 | Bratton et al. | 106/62 X |
| 3,948,813 | 4/1976 | Holcombe, Jr. et al. | 106/57 X |
| 4,126,479 | 11/1978 | Videtto | 106/62 |
| 4,128,433 | 12/1978 | Manning | 106/55 |
| 4,152,234 | 5/1979 | Pollner | 204/195 S |
| 4,155,828 | 5/1979 | Takao et al. | 204/195 S |
| 4,183,798 | 1/1980 | Esper et al. | 204/195 S |

*Primary Examiner*—Arthur C. Prescott
*Attorney, Agent, or Firm*—Sughrue, Rothwell, Mion, Zinn and Macpeak

[57] ABSTRACT

An oxygen sensor is composed of or contains a composite solid electrolyte material and, optionally, a body of a non-conducting ceramic material. The composite solid electrolyte material comprises a mixture of at least two constituents, one of which is a good oxygen ion conductor and the other a non-electrolyte ceramic. Magnesium aluminate spinel may be used for the non-conducting ceramic material in the composite solid electrolyte and for the body of the oxygen sensor.

12 Claims, No Drawings

OXYGEN SENSORS

This invention relates to sensors incorporating solid electroyle materials which are used to measure the oxygen potential in high temperature gases, molten metals and molten glasses, and is an improvement in, or modification of, the invention disclosed in our parent Australian Patent Specification No. 31250/77.

In our parent specification we disclosed an oxygen sensor composed of or containing a composite solid electrolyte material comprising an intimate mixture of fine particles of at least one oxygen ion conductor selected from doped thoria and stabilized, or partially stabilized, zirconia or hafnia, and a non-electrolyte ceramic material selected from alumina, aluminous porcelain and mullite. By appropriately choosing the proportions of the electrolyte and non-electrolyte constituents of the composite solid electrolyte material, there could be produced a strong material having both satisfactory electrolyte properties and a thermal expansion coefficient close to that of nonelectrolyte ceramic materials used, in some embodiments of the design, for the body of the oxygen sensors.

We have now found that magnesium aluminate spinel (ideal formula $MgAl_2O_4$) is stable in the presence of oxygen ion conductors of the type disclosed in the above-mentioned patent specification and also has a close thermal expansion match to the composite solid electrolyte material disclosed in our said patent specification. It may therefore be used as the non-electrolyte ceramic material in either (or both) sensor to permit the fabrication of crack-free, leak-tight sensors of the "active tip" type by both fusion welding and green-forming techniques. The combination of the magnesium aluminate spinel body and a scandia-stabilized, or partially stabilized, zirconia plus alumina tip is particularly suitable for low temperature applications (such as in automobiles) because of the excellence of the thermal expansion match, the high ionic conductivity of the scandia-stabilized zirconia, and the thermodynamic stability of the spinel/composite electrolyte interface. Scandia-stabilized zirconia is known to have the highest ionic conductivity of any of the stabilized zirconias.

While scandia-stabilized zirconia is of particular interest for this modification of our parent invention, for the reasons previously stated, zirconia or hafnia, stabilized or partially stabilized with other rare earth oxides or with yttria, or doped thoria, may also be used as the oxygen ion conducting phase in the composite solid electrolyte material in place of scandia-stabilized zirconia.

Accordingly, one aspect of the present invention provides an oxygen sensor comprising a pair of electrodes separated by a composite solid electrolyte material, wherein said composite solid electrolyte material consists of 25 to 75% by vol. of an oxygen ion conductor and 75 to 25% by vol. of magnesium aluminate spinel.

A further aspect of the present invention provides an oxygen sensor comprising a ceramic hollow body with one electrode located within said body and another electrode located outside said body, said electrodes being separated from one another by a composite solid electrolyte material comprising a minor portion of the ceramic hollow body; wherein said composite solid electrolyte material consists of 25 to 75% by vol. of an oxygen ion conductor and 75 to 25% by vol. of a non-electrolyte material selected from the group consisting of alumina, aluminous porcelain, mullite and magnesium aluminate spinel; and wherein the major portion of the ceramic hollow body consists of magnesium aluminate spinel.

Preferably, the microstructure of the composite solid electrolyte material consists of an intimate mixture of fine grains of the components.

The oxygen ion conductor is preferably a material selected from the group consisting of doped thoria, stabilized and partially stabilized zirconia and hafnia, and mixtures thereof. Scandia is the preferred stabilizer.

The magnesium aluminate spinel used in the composite solid electrolyte material may incorporate an excess of MgO or $Al_2O_3$ to control the strength and hardness of the spinel and to modify its thermal expansion coefficient. Suitable compositions vary within the range of 40 mole % MgO/60 mole % $Al_2O_3$ to 55 mole % MgO/45 mole % $Al_2O_3$.

The spinel powder may be prepared by blending alumina and magnesium carbonate powders in the required proportions, pre-reacting at 1100° C. for one hour in air, and sieving through 100 mesh screens. The solid electrolyte materials may be prepared as described in the parent specification.

Preferably, the content of the conducting constituent(s) in the composite solid electrolyte material is from about 30 to about 60 percent by volume. More preferably, it is from 30 to 50 percent by volume.

An oxygen probe made in accordance with the present invention with a pellet, disc or small tip region of composite solid electrolyte fusion sealed or otherwise bonded to or formed in the end of a body of magnesium aluminate spinel will normally have the probe electrodes mounted to enable the electrical potential across the pellet, disc or tip to be measured. The alternative sensor construction, with the composite electrolyte formed into a hollow body, will again have, usually, the conventional construction of one electrode mounted in contact with the inner surface of the sensor, and the other electrode in contact with the outer surface of the sensor. A protective sheath may be provided around each form of sensor, with apertures to allow the fluid under investigation to contact the outer surface of the composite solid electrolyte. Such a protective sheath may, in some cases, be the outer or forward electrode of the probe.

The following examples illustrate the preparation and properties of (a) the magnesium aluminate spinel used for the sensor body, (b) the composite solid electrolyte material of the sensor tip incorporating magnesium aluminate spinel, and (c) complete oxygen sensors which use magnesium aluminate spinel in either the composite solid electrolyte material or the body of the sensor.

EXAMPLE 1

Three magnesium aluminate spinel bars having the compositions: 50 mol % MgO—50 mol % $Al_2O_3$, 40 mol % MgO—60 mol % $Al_2O_3$, and 55 mol % MgO—45 mol % $Al_2O_3$, were prepared by blending alumina and magnesium carbonate powders, prereacting at 1100° C. for one hour in air, sieving through 100 mesh screens, isopressing at 30,000 psi and firing for 15 hours at 1700° C. in air. Thermal expansion was measured in a dilatometer over the range room temperature to 1500° C. and was found to agree closely with the expansion curves previously obtained for various composite solid electrolyte mixtures based on alumina as the diluent and yttria- or scandia-stabilized zirconia as the conducting phase. The best agreement was with the scandia-stabilized zirconia composite electrolytes.

EXAMPLE 2

Three composite bars approximately 5 mm in diameter and approximately 60 mm long with one half length of each comprised of one of the magnesium aluminate spinels of Example 1 and the other half of each comprised of 60 vol % $Al_2O_3$ and 40 vol % [$ZrO_2$+7 mol % $Sc_2O_3$] were prepared. These bars were isopressed at 30,000 psi and fired at 1700° C. for 15 hrs. in air. After firing, the bars were sound and crack-free, with no tendency to separate at the interfaces between the various spinels and the composite solid electrolyte. This experiment confirmed that the thermal expansion match was sufficient to avoid cracking, and showed that there was no problem associated with reactions across the spinel/electrolyte interface during firing.

EXAMPLE 3

Three "pellet-in-tube" fusion-bonded sensors were made using Degussit SP23 commercial spinel tubing 5 mm inside diameter and 8 mm outside diameter, and pellets of 60 vol % $Al_2O_3$—40 vol % ($ZrO_2$+7 mol % $Sc_2O_3$). These seals proved to be completely leak-tight to a conventional 30 psi air internal pressurization test, and thus were better than the seals normally produced in alumina tubing.

EXAMPLE 4

Composite solid electrolyte pellets for use in oxygen sensors were made from mixtures of magnesium aluminate spinel powder as prepared in Example 1 and a prereacted mixture of unstabilized zirconia powder and scandia powder. The scandia content was sufficient to yield a stabilized zirconia containing 7 mole percent $Sc_2O_3$, and prereaction was achieved by calcining at 1100° C. for one hour.

The pellets contained 40 vol % [$ZrO_2$+7 mol % $Sc_2O_3$] and 60 vol % spinel. They were densified by sintering in air at 1700° C. for 15 hours.

The fired pellets were characterized by x-ray diffraction, optical microscopy and the measurement of density, electrical resistance and thermal expansion. All these properties suggested that the composite solid electrolyte material was suitable for making oxygen sensors of the "active tip" type. The pellets were successfully fusion sealed into alumina tubing.

EXAMPLE 5

A short tube for use as an oxygen sensor, having a magnesium aluminate spinel body and a tip of 60 vol % $Al_2O_3$—40 vol % ($ZrO_2$+7 mol % $Sc_2O_3$), was made by isostatic pressing around a metal mandrel located concentrically within a rubber bag liner in a vented plastic tube. The general description of the isostatic pressing technique for making "active tip" sensors is given in the aforementioned parent patent specification No. 31250/77 (Example 12 thereof). After extraction of the mandrel the tube was densified to a sound body by firing at 1750° C. for 5 hours.

The sensors made as described in Examples 3, 4 and 5 were evaluated by determining the vacuum leak rate at 700° to 1200° C. and the cell voltages at 700° to 1300° C. for the conditions air versus air, air versus oxygen, and air versus various $CO/CO_2$ mixtures from 5 volume percent CO and 95 volume percent $CO_2$ to 99 volume percent CO and 1 volume percent $CO_2$. Platinum paste electrodes were used for the cell voltage tests. The cell voltages were compared with the ideal values given by the Nernst relationship, $$E = \frac{RT}{nF} \cdot \ln \frac{[PO_2 \text{ (reference gas)}]}{[PO_2 \text{ (test gas)}]}$$

where
  E = the cell voltage
  R = the gas constant
  T = the absolute temperature
  n = 4 (the number of electrons transferred per oxygen molecule)
  F = the value of the Faraday constant, and
  $PO_2$ = the oxygen partial pressure.

Compared with the sensors made as described in our parent Australian Patent Specification No. 31250/77 the vacuum leak rate was lower and the cell voltages were identical within ± 1 mV. Both the sensors of these examples and the sensors of Australian Patent Specification No. 31250/77 gave cell voltages which obeyed the Nernst relationship within ± 2 mV in oxygen, air and air/nitrogen mixtures at 700° to 1300° C., and in $CO/CO_2$ mixtures at 900° to 1300° C. All sensors could therefore be used to measure the equilibrium oxygen partial pressure in a wide range of both oxidising and reducing gas mixtures.

Those skilled in the art will appreciate that the invention described herein is susceptible to variations and modifications other than those specifically described. It is to be understood that the invention includes all such variations and modifications which fall within its spirit and scope.

We claim:

1. In an oxygen sensor comprising a pair of electrodes separated by a composite solid electrolyte material comprising an oxygen ion conductor, the improvement wherein said composite solid electrolyte material consists of 25 to 75% by vol. of oxygen ion conductor and 75 to 25% by vol. of magnesium aluminate spinel.

2. An oxygen sensor as defined in claim 1, wherein the oxygen ion conductor is selected from the group consisting of doped thoria, stabilized and partially stabilized zirconia and hafnia, and mixtures thereof.

3. In an oxygen sensor comprising a ceramic hollow body with one electrode located within said body and another electrode located outside said body, said electrodes being separated from one another by a composite solid electrolyte material comprising an oxygen ion conductor and being a minor portion of the ceramic hollow body; the improvement wherein the major portion of the ceramic hollow body consists of magnesium aluminate spinel, and wherein said composite solid electrolyte material consists of 25 to 75% by vol. of oxygen ion conductor and 75 to 25% by vol. of a non-electrolyte material selected from the group consisting of alumina, aluminous porcelain, mullite and magnesium aluminate spinel.

4. An oxygen sensor as defined in claim 3 wherein the oxygen ion conductor is selected from the group consisting of doped thoria, stabilized and partially stabilized zirconia and hafnia, and mixtures thereof.

5. An oxygen sensor as defined in any one of the preceding claims, wherein the content of the oxygen ion

5 conductor in the composite solid electrolyte material is from 30 to 60 percent by volume.

6. An oxygen sensor as defined in any one of claims 1-4, wherein the content of the oxygen ion conductor in the composite solid electrolyte material is from 30 to 50 percent by volume.

7. As oxygen sensor as defined in any one of claims 1-4, wherein the composition of the magnesium aluminate spinel is within the range from 40 mole percent MgO plus 60 mole percent $Al_2O_3$ to 55 mole percent MgO plus 45 mole percent $Al_2O_3$.

8. An oxygen sensor as defined in claim 1 or claim 2 wherein the composite solid electrolyte material is in the form of a closed tube.

9. An oxygen sensor as defined in any one of claims 1-4, wherein the composite solid electrolyte material is in pellet or disc form, bonded in or to the end of an open tube of magnesium aluminate spinel.

10. An oxygen sensor as defined in claim 9, in which the composite solid electrolyte pellet or disc is joined to the tube by fusion sealing.

11. An oxygen sensor as defined in claim 3, formed in the "green" or unfired state so that the composite solid electrolyte material forms a conducting region in a magnesium aluminate spinel hollow body, then fired.

12. An oxygen sensor as defined in any one of claims 1-4 in which the composite solid electrolyte material is composed of a mixture of alumina and zirconia stabilized or partially stabilized with scandia.

* * * * *

UNITED STATES PATENT AND TRADEMARK OFFICE
CERTIFICATE OF CORRECTION

PATENT NO. : 4,240,891

DATED : December 23, 1980

INVENTOR(S) : Michael John Bannister

It is certified that error appears in the above—identified patent and that said Letters Patent is hereby corrected as shown below:

Col. 6, Claim 12, line 2, delete "1-4" and insert therefor -- 3 or 4 --.

Signed and Sealed this

Nineteenth Day of January 1982

[SEAL]

Attest:

Attesting Officer

GERALD J. MOSSINGHOFF

Commissioner of Patents and Trademarks